(12) United States Patent
Pollack et al.

(10) Patent No.: US 8,930,147 B2
(45) Date of Patent: Jan. 6, 2015

(54) MULTI-SENSOR PATCH AND SYSTEM

(75) Inventors: Richard S. Pollack, Boulder, CO (US); Joseph Michael Letkomiller, Thornton, CO (US); Wade W. Webster, Woodinville, WA (US); Scott D. Dalgleish, Boulder, CO (US); Donald E. Kirkpatrick, Denver, CO (US)

(73) Assignee: Prima-Temp, Inc., Boulder, CO (US)

( * ) Notice: Subject to any disclaimer, the term of this patent is extended or adjusted under 35 U.S.C. 154(b) by 1005 days.

(21) Appl. No.: 13/021,806

(22) Filed: Feb. 7, 2011

(65) Prior Publication Data

US 2011/0213559 A1 Sep. 1, 2011

Related U.S. Application Data

(60) Provisional application No. 61/301,808, filed on Feb. 5, 2010.

(51) Int. Cl.

| | |
|---|---|
| *G06F 19/00* | (2011.01) |
| *G05B 23/02* | (2006.01) |
| *A61B 5/00* | (2006.01) |
| *G01K 1/02* | (2006.01) |
| *G01K 13/00* | (2006.01) |

(52) U.S. Cl.
CPC .......... *G05B 23/0221* (2013.01); *A61B 5/0008* (2013.01); *G01K 1/024* (2013.01); *G01K 13/002* (2013.01); *G06F 19/3412* (2013.01)
USPC .......................................................... 702/19

(58) Field of Classification Search
CPC ............ G06F 19/3418; G06F 19/3406; G06F 19/345; A61B 5/681
USPC .................... 702/19, 117, 118, 182–185, 188
See application file for complete search history.

(56) References Cited

U.S. PATENT DOCUMENTS

2014/0104059 A1\* 4/2014 Tran .......................... 340/539.12

\* cited by examiner

*Primary Examiner* — Edward Raymond
(74) *Attorney, Agent, or Firm* — Santangelo Law Offices, P.C.

(57) ABSTRACT

Embodiments of the invention provide systems and methods for remote sensing and/or monitoring utilizing a sensing device, such as may be implemented in a patch that can be placed on or affixed to a subject, where the sensing device includes multiple sensors. For example, one embodiment of the present invention includes a wireless human temperature skin patch providing accurate measurement of human temperature from a sensing device applied to the skin and even in the presence of differing ambient temperature. In such an embodiment, the patch can include, for example, a flexible, breathable bandage or adhesive strip or pad to affix the sensing device to a patient. The sensing device can include multiple sensors such as two or more temperature sensors that can be used to accurately determine the patient's core body temperature from the measured temperature at the skin.

8 Claims, 9 Drawing Sheets

MULTI-SENSOR PATCH AND SYSTEM

CROSS-REFERENCES TO RELATED APPLICATIONS

The present application claims benefit under 35 USC 119(e) of U.S. Provisional Application No. 61/301,808, filed on Feb. 5, 2010 by Pollack et al. and entitled "Multi-Sensor Patch," of which the entire disclosure is incorporated herein by reference for all purposes.

BACKGROUND OF THE INVENTION

Embodiments of the present invention relate generally to methods and systems for remote sensing and more particularly to remote sensing and/or monitoring utilizing a sensing device, such as may be implemented in a patch that can be placed on or affixed to a subject, where the sensing device includes multiple sensors.

A variety of different remote sensors are used in a wide range of applications such as manufacturing, transportation, facilities management, security, health care, etc. For example, in a health care setting, remote sensors are commonly used for measuring bodily parameters of a patient such as heart rate, blood pressure, blood oxygen level, respiration rate, and core temperature. Many of these sensors are applied externally to the patient's skin.

Previous methods and systems for determining a patient's core temperature from a measurement at the skin assume to calculate an accurate core temperature when a single sensor on a patient's skin is well insulated from the ambient temperature. Other previous methods assume to calculate an accurate core temperature by having a first sensor directly on the skin and a second sensor on the upper surface of a patch, and by heating the upper sensor until it has a temperature equal to the skin sensor, and assuming that this temperature equals core temperature. Another previous method assumes to calculate an accurate core temperature by having a first sensor directly on the skin and a second sensor on the upper surface of a patch and then by using an algorithm that calculates the core temperature based on the difference in the temperature between the two sensors.

These previous methods that use skin surface temperature and ambient temperature need to use algorithms that assume the temperature gradient from a human's core to their skin is identical. This assumption of identical temperature gradient through the body mass will introduce errors in the reported core temperature due to the variation of size, weight, and body type of different people. Furthermore, human temperature measurement done by an electronic patch applied to the skin can be in error when a temperature measuring component is at a different temperature than the skin due to poor thermal contact or due to a gradient across the patch caused by ambient temperature.

In other applications and with other types of sensors, similar problems can affect the measurements made by the sensor. That is, when utilizing an externally applied sensor for measuring a metric, a variety of ambient influences can adversely affect the accuracy and/or reliability of the sensor. Hence, there is a need for improved methods and systems for remote sensing and/or monitoring utilizing a sensing device.

BRIEF SUMMARY OF THE INVENTION

Embodiments of the invention provide systems and methods for remote sensing and/or monitoring utilizing a sensing device. More specifically, embodiments of the present invention provide methods and systems for utilizing a sensing device, such as may be implemented in a patch that can be placed on or affixed to a subject, where the sensing device includes multiple sensors. According to one embodiment, a method can comprise receiving sensor data from a sensing device. The sensing device can comprise a plurality of sensors and the sensor data can include data from each of the plurality of sensors. The received sensor data from each of the plurality of sensors can be compared to the received sensor data for others of the plurality of sensors. The received sensor data can also be compared to a saved set of previously received sensor data. A determination can be made as to whether the received sensor data is reliable based on comparing the received sensor data from each of the plurality of sensors to the received sensor data for others of the plurality of sensors and comparing the received sensor data to the saved set of previously received sensor data. In response to determining the received sensor data is not reliable, the received sensor data may be discarded. In response to determining the received sensor data is reliable, the received sensor data may be saved, e.g., in a profile.

In some cases, comparing the received sensor data to a saved set of previously received sensor data can comprise comparing a rate of change of the received sensor data. The rate of change of the received sensor data can also be compared to a rate of change recorded in the profile. A determination of an occurrence of an event can be made based on comparing the rate of change of the received sensor data to the rate of change recorded in the profile. For example, the plurality of sensors can comprise temperature sensors and the sensing device can be affixed to a human patient. In such cases, the event can comprise an onset of a fever.

According to another embodiment, a system for measuring a temperature of a subject can comprise a patch including a sensing device with a microcontroller, a wireless transmitter, and a plurality of sensors. The plurality of sensors can include as least a first temperature sensor and a second temperature sensor. A supporting system including a memory, a processor, and a wireless receiver can be communicatively coupled with the transmitter of the sensing device. The memory of the supporting system can include a series of instructions which, when executed by the processor, cause the supporting system to receive sensor data from a sensing device. The sensor data can include data from each of the first temperature sensor and the second temperature sensor. The supporting system can compare the received sensor data from the first temperature sensor to the received sensor data from the second temperature sensor, compare the received sensor data to a saved set of previously received sensor data, and determine whether the received sensor data is reliable based on comparing the received sensor data from the first temperature sensor to the received sensor data from the second temperature sensor and comparing the received sensor data to the saved set of previously received sensor data.

Comparing the received sensor data to a saved set of previously received sensor data can comprise comparing a rate of change of the received sensor data. The supporting system can also compare the rate of change of the received sensor data to a rate of change recorded in a profile. The supporting system can then determine an occurrence of an event based on comparing the rate of change of the received sensor data to the rate of change recorded in the profile. For example, the patch may be affixed to a human patient and the event can comprise an onset of a fever.

In some cases, the system can further comprise a reader device communicatively coupled with the sensing device via the wireless transmitter of the sensing device. The reader device can receive temperature data from the sensing device. Additionally or alternatively, the reader device can communicate commands to the sensing device and/or provide the temperature data to the supporting system.

According to yet another embodiment, a machine-readable medium can have stored thereon a series of instructions which, when executed by a processor, cause the processor to handle sensor data from a multi-sensor device by receiving sensor data from the multi-sensor device. The sensor data can include data from at least a first temperature sensor and a second temperature sensor. The received sensor data from the first temperature sensor can be compared to the received sensor data from the second temperature sensor. The received sensor data can also be compared to a saved set of previously received sensor data. A determination can be made as to whether the received sensor data is reliable based on comparing the received sensor data from the first temperature sensor to the received sensor data from the second temperature sensor and comparing the received sensor data to the saved set of previously received sensor data.

In some cases, comparing the received sensor data to a saved set of previously received sensor data can comprise comparing a rate of change of the received sensor data. The rate of change of the received sensor data can also be compared to a rate of change recorded in the profile. In such cases, a determination of an occurrence of an event can be made based on comparing the rate of change of the received sensor data to the rate of change recorded in the profile.

DETAILED DESCRIPTION OF THE INVENTION

Figure 1A:
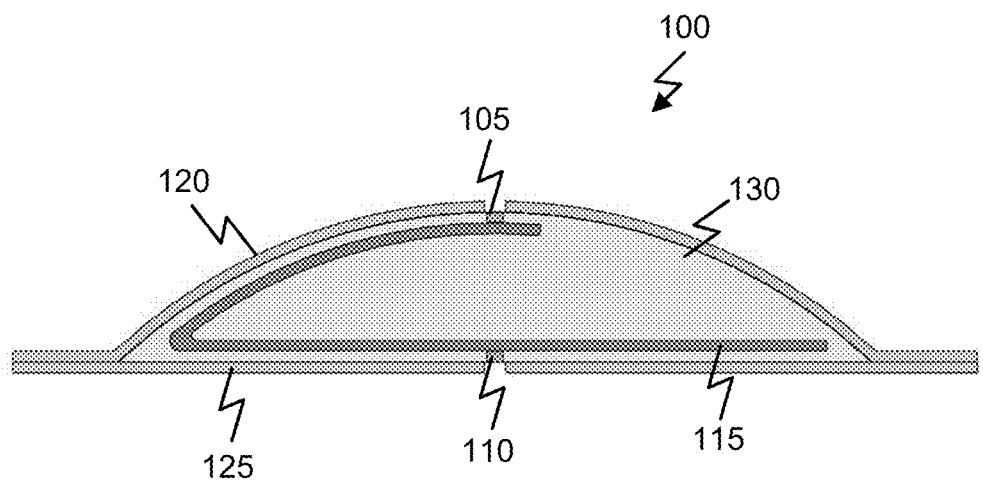
FIGS. 1A and 1B illustrate elements of a multi-sensor patch according to one embodiment of the present invention.

In the following description, for the purposes of explanation, numerous specific details are set forth in order to provide a thorough understanding of various embodiments of the present invention. It will be apparent, however, to one skilled in the art that embodiments of the present invention may be practiced without some of these specific details. In other instances, well-known structures and devices are shown in block diagram form.

The ensuing description provides exemplary embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "machine-readable medium" includes, but is not limited to portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Embodiments of the invention provide systems and methods for remote sensing and/or monitoring utilizing a sensing device, such as may be implemented in a patch that can be placed on or affixed to a subject, where the sensing device includes multiple sensors. More specifically, one embodiment of the present invention includes a wireless human temperature skin patch providing accurate measurement of human temperature from a sensing device applied to the skin and even in the presence of differing ambient temperature. In such an embodiment, the patch can include, for example, a flexible, breathable bandage or adhesive strip or pad to affix the sensing device to a patient. The sensing device can include multiple sensors such as two or more temperature sensors that can be used to accurately determine the patient's core body temperature from the measured temperature at the skin.

Embodiments of the present invention assume that the sensor readings are invalid until the one or more sensors near the skin and one or more sensors near the top surface of the of the sensing device naturally migrate to being very close in temperature and the rate of change of the sensors become very near to zero. This natural migration to equal temperatures (elimination of a temperature gradient) and rate of change near zero (skin has warmed to be very near core body temperature) can be due to the patient lying on the sensor against an insulating material, such as a mattress, or sandwiching the sensor between large body parts, such as between the arm and torso. Once the two or more sensors are close to each other in temperature the effect of ambient is eliminated, and once the rate of change of temperature is near zero the body has warmed up the sensor to core body temperature, and the sensor readings can be considered to have a predictable correlation to core temperature. Thus, embodiments of the present invention take out the errors caused by the false assumption of the previous approaches by verifying that the temperature gradient across the patch is very small and the rate of change of the temperature is near zero before considering the measured temperature to be accurate and/or reliable. Although a difference between body core temperature and skin temperature may still exist, this difference is consistent and the data may be used to calculate core temperature. Even in the case where core temperature is not calculated the temperature measured in accordance with this embodiment can be used to calculate an individual patient baseline and also be used to indicate a change from this baseline. Both the calculated core temperature and a change from a baseline are useful for early detection of fevers and infections.

Embodiments of the present invention are based on the understanding that a person's skin warms up slowly when the skin is insulated from the ambient, either by a patient lying on the sensor against an insulating material or sandwiching the sensor between large body parts. Tests show that the temperature of the axilla may take up to forty-five minutes after the arm is held down tightly to reach a steady state and stop rising. It has also been confirmed that when this temperature has reached steady state, it is very near core body temperature, often being higher than carefully conducted oral temperature measurements. Standard patient thermometers, to measure an accurate temperature in the axilla, would need to be held under the arm for this length of time. Therefore, to obtain a reliable temperature manually in the axilla is an uncomfortable and overly restrictive procedure. The patch of this invention can be left on the patient for many days at a time and enables the accurate reading that results from being comfortable to wear for an extended period.

While described herein with reference to temperature sensors, it should be understood that the plurality of sensors implemented in the sensing device can additionally or alternatively include a variety of other sensor types. For example, a patch according to one embodiment can include, in addition to a temperature sensor, a humidity sensor that provides information regarding patient sweating. Together with proper decoding software, this information may be used with temperature data to better diagnose a medical condition. In another embodiment, a sensing device of a patch can include a micro-miniature microphone that, given the proximity of an axially applied patch, can hear the heart beat. This capability may be improved by the fact that when the arm covers the patch it isolates the microphone from noise sources that might prevent the patch from being able to distinguish the heart beat sound. The patch may transmit the heart rate with the temperature data or may only transmit when a change from an established baseline occurs, or when a certain rate of change occurs. Software of the system can combine heart rate information with temperature information to improve the detection of infection or other medical conditions. Furthermore, embodiments of the present invention should not be considered to be limited to healthcare applications. For example, multi-sensor devices can include different types of sensors such vibrations and/or impact sensors, location sensors, pressure sensors, light sensors, flow sensors, etc. used for monitoring equipment, facilities, packages, vehicles, people, animals, etc.

Figure 1B:
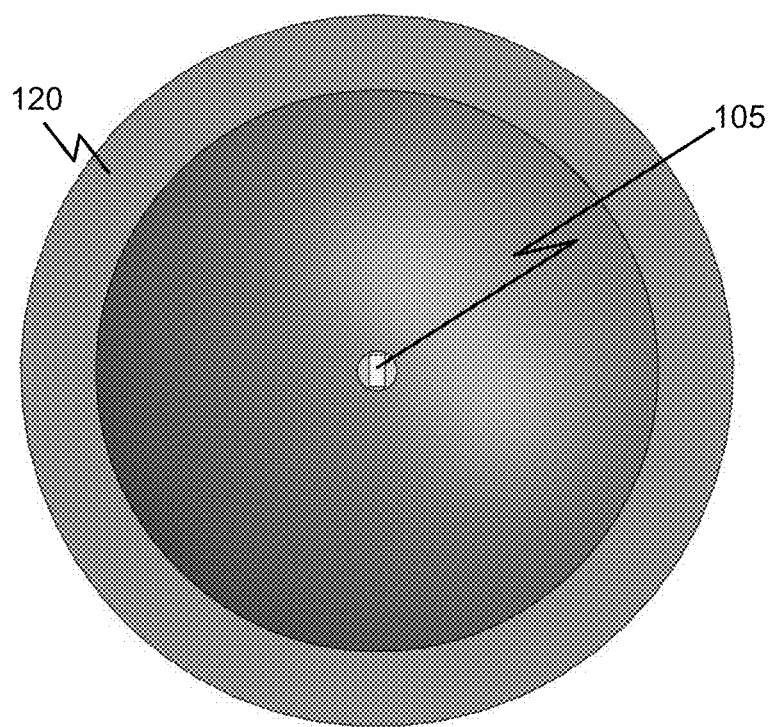

FIGS. 1A and 1B illustrate elements of a multi-sensor patch according to one embodiment of the present invention. More specifically, FIG. 1A illustrates a cross-sectional side view of a multi-sensor patch while FIG. 1B illustrates a top view of the patch. According to one embodiment, a smaller, more accurate and more useful wireless electronic skin surface temperature patch 100, such as illustrated in FIG. 1, can include a sensing device with two or more temperature measurement circuits 105 and 110, a microcontroller (not shown here), a radio transmitter (not shown here), and packaging such as a flex circuit 115 that enables a small, thin, flexible device that can conform to the skin. For example, the patch 100 can include the sensing device adhered to the skin of the patient with a flexible tape or bandage 120 and 125. According to another embodiment, the patch 100 can include the sensing device in conjunction with a pre-made bandage 120 and 125. The bandage 120 and 125 can include a pocket or orifice into which the sensing device can be inserted. The bandage 120 and 125 can be similar to a standard clinical patch including adhesive materials so that it can be attached like a standard bandage. Such a bandage 120 and 125 may comprise a top cover 120 and a bottom layer 125 made of a porous material next to the skin that permits lateral airflow when the arm is raised and temperature is not being measured to reduce issues with sweat accumulating under the patch. According to yet another embodiment, 120 and 125 can be part of the patch itself and be taped onto the patient or subject with standard medical or other tape (not shown).

The sensing device, such as described above, or a system in communication with the sensing device, such as described herein, can use temperature values detected by the multiple temperature sensors to determine when a sensor touching the skin and a sensor near the outer surface of the patch reach the same or nearly the same temperature, indicating that a thermal gradient is not causing an unacceptable error. Waiting until the sensors are naturally at or near the same temperature, such as when the patient is lying on an insulating surface (such as a bed) on his/her back in the case of a patch on the back or their arm is down in the case of a patch applied in the axilla, reduces occurrence of invalid temperature values. That is, when the sensors are at or very near the same temperature the effect of the ambient temperature effect on the reading is significantly reduced if not eliminated.

According to another embodiment, the sensing device can use two or more temperature sensors facing the skin and two or more on the top surface of the patch. The microcontroller in the patch, or the software executing on another system receiving and manipulating the temperature data, can average the value of the sensors, throw out readings that are obviously in error or use only the highest reading, to reduce errors caused by bad skin contact or partial exposure to ambient.

Figure 2:
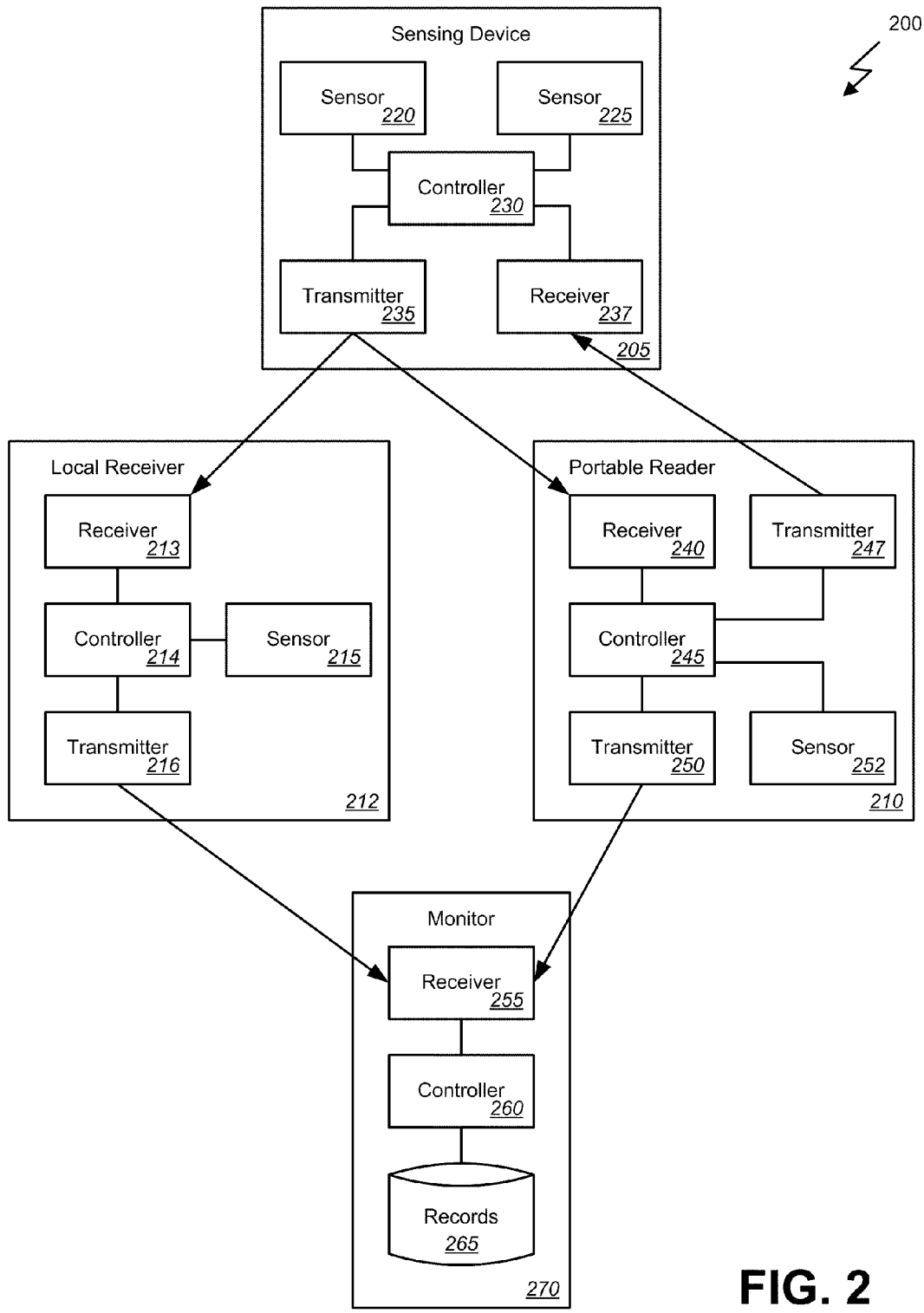
FIG. 2 is a block diagram illustrating components of an exemplary operating environment in which various embodiments of the present invention may be implemented.

FIG. 2 is a block diagram illustrating components of an exemplary operating environment in which various embodiments of the present invention may be implemented. This example illustrates a system 200 utilizing a sensing device 205 including two sensors 220 and 225. As noted above, the sensors 220 and 225 can comprise temperature sensors or any of a number of other types of sensors depending upon the implementation of the system. Optionally, the sensing device 205 can include a receiver 237, such as RFID, near field or other RF receiver that enables the sensing device 205 to receive communication from a reader device 210. Also as noted above, the sensing device 205 itself can be incorporated in a small, thin, and flexible package, i.e., mounted on a flex circuit. For example, in one implementation the sensing device 205 can subtend less than 0.5 square inches of area by utilizing an IC chip that integrates a microprocessor or other controller 230, a beacon radio and a RFID communication circuit 237 or other transmitter 235 into a single IC chip. An example of such a chip is manufactured by EM Microelectronics, part number EM6869. In another implementation, the sensing device 205 can include a microprocessor or other controller 230 and beacon radio or other transmitter 235 in a single IC chip and a second ultra high frequency (UHF) RFID communication IC chip (not shown here) and can subtend less than 0.5 square inches of area by having the UHF RFID communication IC share the same antenna as a UHF beacon radio. An example of such a UHF RFID IC chip is the EM Microelectronics part number EM4325. Such an implementation can include detection and switching circuitry (not shown here) to switch the antenna into the RFID IC chip during RFID function and into the beacon radio circuit during beacon mode.

As noted above, the system 200 utilizing sensing device 205 can include a system 270 in communication with the sensing device 205 and receiving and evaluating the temperature data from the sensing device. Such a system 270 can include a receiver 255, controller 260, and memory 265. This system 270, implemented in a personal computer, laptop, or other computing device as described below with reference to FIG. 3 may receive the temperature data from the sensing device(s) 205 of the patch through the receiver 255. The receiver 255 may communicate with the rest of the system 200 via hardwiring or via a variety of radio transmitter connections, including WiFi and Bluetooth connections. The controller 260 and this system 270 can execute an application for utilizing the received sensor data such as the processes described below with reference to FIGS. 4-9. Based on these processes, the controller 260 may write records of the received sensor data to the memory 265 of the system over time and for a particular subject, i.e., patient, piece of equipment, inventory item, vehicle, etc.

Additionally or alternatively, the system 200 can include a fixed repeater or local receiver device 212. The local receiver device 212 can include a receiver 213 for receiving sensor data transmitted from the sensor device 205. Optionally, the local receiver device 212 may also include a controller, 214 and temperature sensor 252. The sensor 252 in the local receiver device 212 can determine the room ambient temperature. The software can then employ an appropriate algorithm using ambient temperature to improve the sensor device 205 temperature reading even further. Optionally the local receiver device 212 includes a transmitter 216 or other communication channel such as a Bluetooth, WiFi or other RF for communicating with the monitor system 270 or other system or device. In other cases, the local receiver device 212 may include a USB or other port through which sensor data collected by the repeater device may be provided to the monitor system 270 or other system or device.

Additionally or alternatively, the system can include a portable reader device 210. The reader device 210 may be implemented, for example in a Personal Digital Assistant (PDA), cell phone, or other portable computing device. The reader device 210 can include a receiver 240 such as a Bluetooth, RFID or other RF for receiving sensor data transmitted from the sensor device 205 and a controller 245. Optionally, the reader device 210 may also include a transmitter 250 or other communication channel such as a Bluetooth, WiFi, or other RF for communicating with the monitor system 270 or other system or device. In other cases, the reader 210 may include a USB or other port through which sensor data collected by the reader device may be provided to the monitor system 270 or other system or device. Similar to the local receiver device 212, reader device 210 can employ a temperature sensor 252 in the reader that is in communication with the system software executing on either the reader device 210 or the monitor system 215. The sensor 252 in the reader device 210 can determine the room ambient temperature. The software can then employ an appropriate algorithm using ambient temperature to improve the sensor device 205 temperature reading even further.

Optionally the reader device 210 may include transmitter 247 that communicates with the sensing device 205 via a Bluetooth, Near Field Communication (NFC), Radio Frequency Identification (RFID), or other connection. As further described below, this communication link permits the Reader 210 to query the sensing device 205 to cause it to transmit data immediately, allowing real time reading of the sensor data, and further enables programming or turning on or off the sensing device 205.

According to one embodiment, the sensing device 205 can encrypt the temperature data prior to transmission to the system 215, local receiver device 212 or the reader 210. For example, the controller 230 of the sensing device 205 can use the AES standard to eliminate unauthorized decoding of patient data and enable conformance to privacy and confidentiality requirements.

A sensing device 205 as described herein, together with a supporting system 215 and/or reader 210 and/or local receiver device 212, can support a number of different communication modes. For example, a sensing device 205 and system 200 can support: 1) a beacon mode RF transmission, for example in the UHF frequency range, which transmits to a receiver, e.g., 10 feet or more away, at regular, programmable intervals, say once every five minutes; 2) transmits when a temperature change beyond a set threshold occurs (alarm). This threshold may be based on each individual's baseline instead of a pre-established temperature. In some cases, a sensing device can include a proximity, RFID type communication link in addition to the beacon transmission. This RFID link enables a real-time inquiry function which can be achieved by adding a low frequency, high frequency or ultra-high frequency antenna and RFID read/write circuit 237 that is in communication with the sensing device controller 230. This link can permit, for example: a proximity real-time inquiry from a hand-held device (such as Reader 210); turning on the sensing device from a proximity handheld device to eliminate a switch for turning on the sensing device prior to being inserted into a bandage of the patch and/or attached to the patient; assigning the patient ID number, room number, account number, admitting nurse, etc. to the sensing device so that this data can be integrated with care and billing systems; programming of alarm thresholds and transmit interval at point of application; and other functions. In some implementations, the sensing device 205 can log temperature readings and time/date into memory for later retrieval (data logger) via the real-time inquiry mode. This allows, for example, a record of the recent past to be evaluated by an attending nurse near the patient. One embodiment can include a sensing device with an ultra low energy Bluetooth circuit that serves as the proximity inquiry link. This can allow proximity inquiry and programming to be done by a mobile device such as a smart phone equipped with Bluetooth functionality. Another option is that both the Reader 210 proximity communication and the beacon function are via Bluetooth.

As noted above, it should be understood that the plurality of sensors implemented in the sensing device can additionally or alternatively include a variety of other sensor types. For example, a patch according to one embodiment can include, in addition to a temperature sensor, a humidity sensor that provides information regarding patient sweating. Together with proper decoding software, this information may be used with temperature data to better diagnose a medical condition. In another embodiment, a sensing device of a patch can include a micro-miniature microphone that, given the proximity of an axially applied patch, can hear the heart beat. This capability may be improved by the fact that when the arm covers the patch it isolates the microphone from noise sources that might prevent the patch from being able to distinguish the heart beat sound. The patch may transmit the heart rate with the temperature data or may only transmit when a change from an established baseline occurs, or when a certain rate of change occurs. Software of the system can combine heart rate information with temperature information to improve the detection of infection or other medical conditions.

Figure 3:
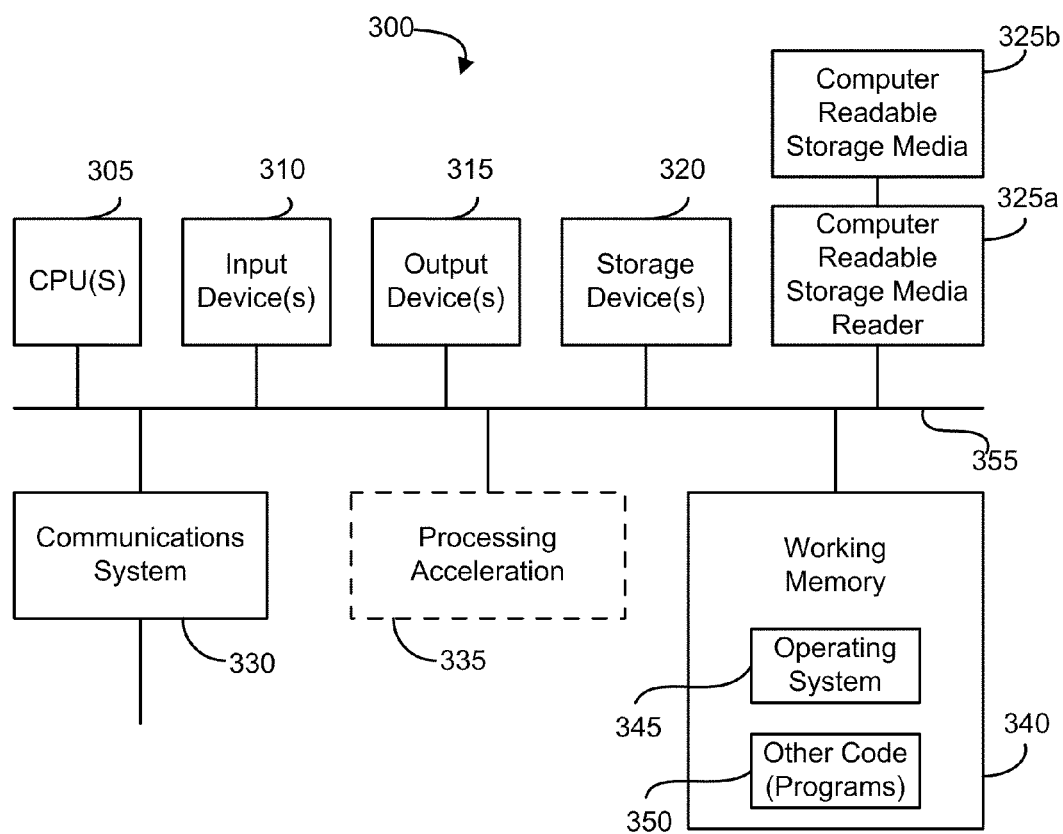
FIG. 3 is a block diagram illustrating an exemplary computer system in which embodiments of the present invention may be implemented.

FIG. 3 is a block diagram illustrating an exemplary computer system in which embodiments of the present invention may be implemented. As noted, a system in which the patch described herein may be implemented can include a reader, handheld device, and/or supporting system with any or all executing software for receiving, storing, and or manipulating temperature data from the sensing device of the patch. FIG. 3 illustrates one such exemplary computer system 300. The system 300 may be used to implement any of the supporting system, reader, handheld device, etc. described above. The computer system 300 is shown comprising hardware elements that may be electrically coupled via a bus 355. The hardware elements may include one or more central processing units (CPUs) 305, one or more input devices 310 (e.g., a mouse, a keyboard, etc.), and one or more output devices 315 (e.g., a display device, a printer, etc.). The computer system 300 may also include one or more storage device 320. By way of example, storage device(s) 320 may be disk drives, optical storage devices, solid-state storage device such as a random access memory ("RAM") and/or a read-only memory ("ROM"), which can be programmable, flash-updateable and/or the like.

The computer system 300 may additionally include a computer-readable storage media reader 325a, a communications system 330 (e.g., a modem, a network card (wireless or wired), an infra-red communication device, etc.), and working memory 340, which may include RAM and ROM devices as described above. In some embodiments, the computer system 300 may also include a processing acceleration unit 335, which can include a DSP, a special-purpose processor and/or the like.

The computer-readable storage media reader 325a can further be connected to a computer-readable storage medium 325b, together (and, optionally, in combination with storage device(s) 320) comprehensively representing remote, local, fixed, and/or removable storage devices plus storage media for temporarily and/or more permanently containing computer-readable information. The communications system 330 may permit data to be exchanged with the network 320 and/or any other computer described above with respect to the system 300.

The computer system 300 may also comprise software elements, shown as being currently located within a working memory 340, including an operating system 345 and/or other code 350, such as an application program (which may be a client application, web browser, mid-tier application, RDBMS, etc.). It should be appreciated that alternate embodiments of a computer system 300 may have numerous variations from that described above. For example, customized hardware might also be used and/or particular elements might be implemented in hardware, software (including portable software, such as applets), or both. Further, connection to other computing devices such as network input/output devices may be employed. Software of computer system 300 may include code 350 for implementing embodiments of the present invention as described herein.

As noted, software of the system 300 can receive, store, and/or manipulate temperature data from the sensing device of the patch. For example, the software can include algorithms that compensate for the difference in skin and core temperature to report a core temperature. In another example, the software can include algorithms that filter the individual temperature measurements to report an actual temperature and to establish a unique baseline for each patient. Additionally or alternatively, the software can alert of a fever based on an increase from an individual baseline versus an arbitrary temperature such as 102 degrees F. In some embodiments, the software can provide a diagnosis of possible infection type based on the trend of temperature changes versus a baseline temperature. In yet another example, the software may monitor the difference between the sensors and the rate of change of the temperature to: assess the reliability of the measurement; predict a final temperature sooner than waiting for equilibration by extrapolating a changing temperature; detect if a person is moving or has left a bed; etc. The software may additionally or alternatively include algorithms that add room ambient temperature from a receiver in the room to the temperature readings from sensors to improve the accuracy of reading. Depending upon the exact implementation, the software may provide integration with a hospital or clinic IT system, or may be designed as a stand-alone system without such integration.

Figure 4:
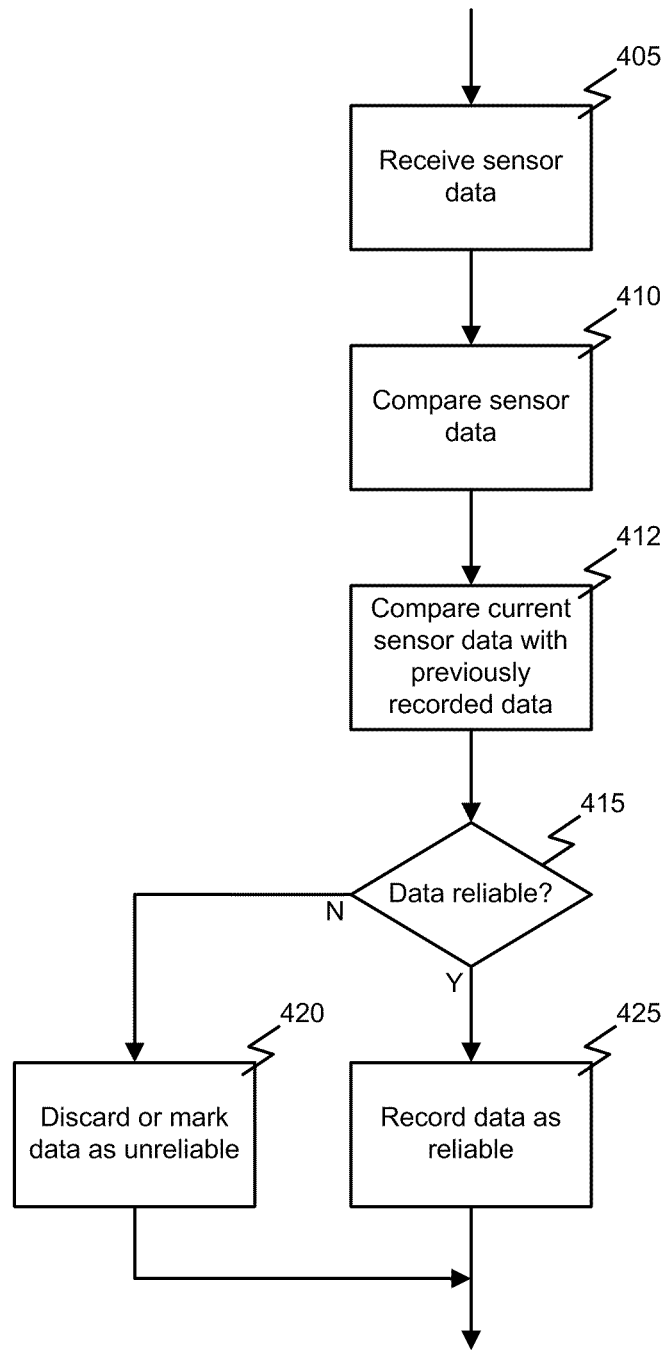
FIG. 4 is a flowchart illustrating an exemplary process for remote sensing using a multi-sensor device according to one embodiment of the present invention.

FIG. 4 is a flowchart illustrating an exemplary process for remote sensing using a multi-sensor device according to one embodiment of the present invention. In this example, processing begins with receiving sensor data from two or more sensors of a sensing device as described above. The sensor data can be compared 410, one to the others. Further, the sensor data 405 can be compared with previous readings 412 to determine if the readings have achieved a steady state. Based on these comparisons 410 and 412, a determination 415 can be made as whether the data is within acceptable limits. For example, the determination 415 can be based on the differences of the sensor data being within some predefined range. If the sensor data is determined 415 to not be within acceptable limits, the data is considered to be unreliable, e.g., not yet stable or otherwise invalid, and can thus be discarded 420. Alternatively, rather than discarding the data, it may be recorded but not relied upon for other purposes, for example for comparison of current and past sensor data 412. If the sensor data is determined to be within acceptable limits and thus reliable, the data can be recorded 425 and/or utilized for monitoring, control, or other purposes.

Embodiments of the present invention that may be directed to measuring temperature of a patient take advantage of the fact that when two body parts are closed together or a large body part is lying on an insulated material such as a mattress, the skin temperature will slowly rise until it is equal or nearly equal to core temperature. This eliminates the effect of ambient temperature. These embodiments take advantage of the fact that when the temperatures from the upper and lower sensors are nearly equal and also at steady state then the skin has warmed up to core temperature and we can reliably read this temperature. A problem with this method is that it takes a long time for the skin to rise to core temperature after it is insulated. This is due to the body's inherent temperature regulation capacity that prevents heat from being rapidly transferred to the skin. This long time interval means that ample opportunity exists for the insulation of the arm or mattress to be lost during movement and therefore long periods of time where the temperature does not achieve steady state. Embodiments of the present invention increase the time during which an accurate core or baseline temperature can be predicted during periods of lost insulation, i.e., during warm up periods.

Figure 5:
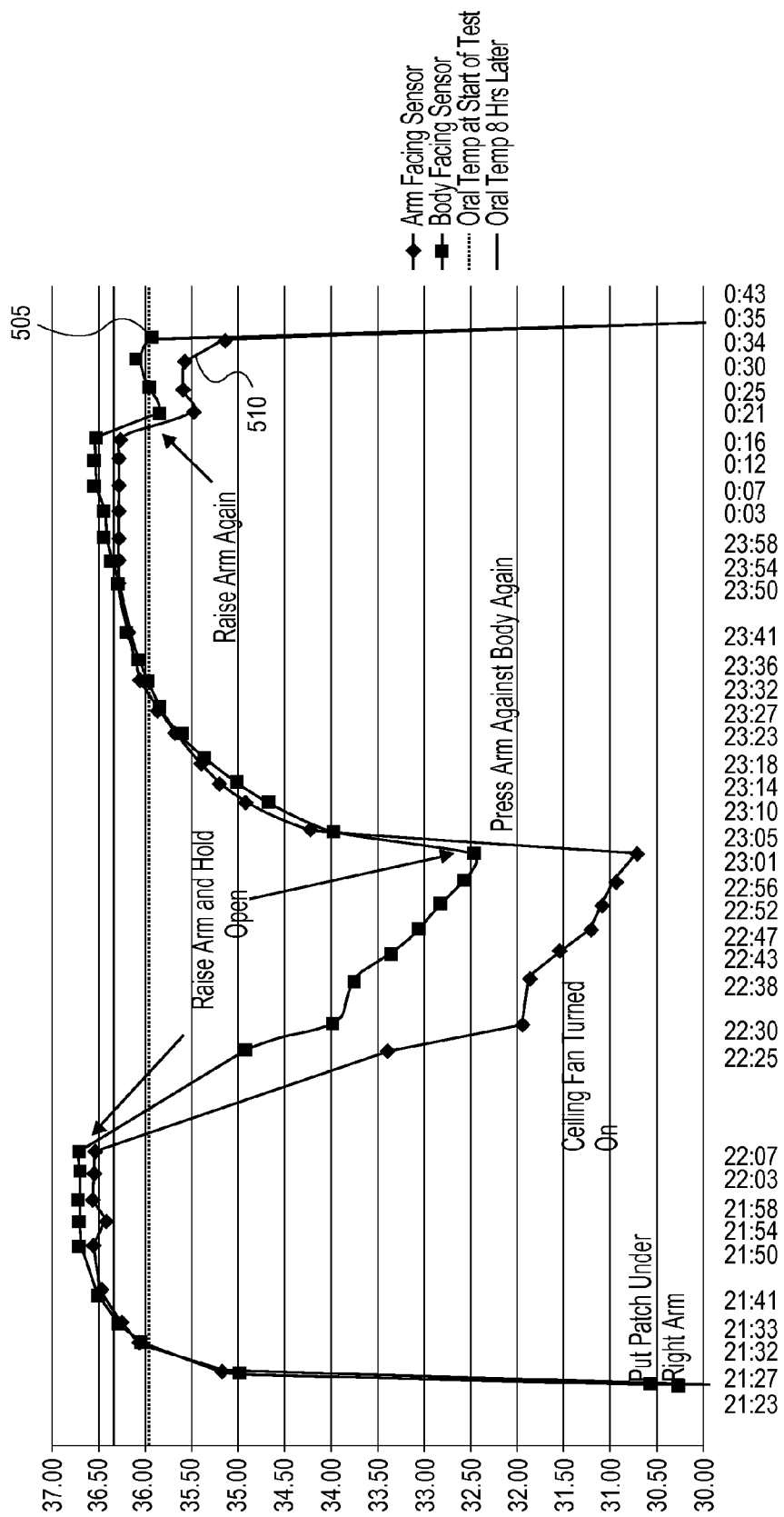
FIG. 5 is a graph illustrating temperatures recorded from a multi-sensor device according to one embodiment of the present invention.

FIG. 5 is a graph illustrating temperatures recorded from a multi-sensor device according to one embodiment of the present invention. More specifically, FIG. 5 is a graph illustrating the recording of temperatures 505 and 510 by the multi-sensor device (one inner sensor (temperature 505) facing the torso (body) and one outer sensor (temperature 510) facing the arm) when placed in the axilla under the right arm. Temperatures 505 and 510 are recorded over a period of time during which the right arm is alternately raised and lowered. As can be seen, the temperatures 505 and 510 measured by the both sensors increased to a measurably steady state temperature over a period of time after the arm is lowered. In several such tests it was observed that this steady state temperature is reached from 30 to 45 minutes after a raised arm is lowered. If the arm is raised for only a brief period when the temperature is near or at steady state, the temperature drops only slightly and then again reaches steady state in a shorter period of time. If the sensors are well insulated with clothing or bedding, the temperature drop when the arm is raised can be much lower than in open air and the resulting time for the temperature to rise to steady state after the arm is lowered can be much shorter. This pattern of small temperature drops and short warm up periods is typical of temperature measurements patch worn in the axilla or one that is insulated by being between the body and a mattress. One thing to note, and one of the main reasons for 2 sensors, is that when the arm is very slightly closed, such as when typing on a computer, the inner and outer sensors can reach steady state, but be lower than core temperature (they are being slightly cooled). In this case the differential between the two sensors will be greater than 0.25° C.

A baseline core temperature is recorded by the body facing sensor when the difference between the two sensor readings is less than some predetermined differential and when, at the same time, the change between consecutive readings (slope) is below some predetermined value. An example of these predetermined values is 0.25° C. and the change in both sensor readings is less than 0.03° C. per minute. (i.e., both inner and outer sensors are at near steady state). Note that the temperature measured in the axilla in this example is higher than the orally measured temperature, indicating that the measured temperature is at or very near core body temperature.

Figure 6A:
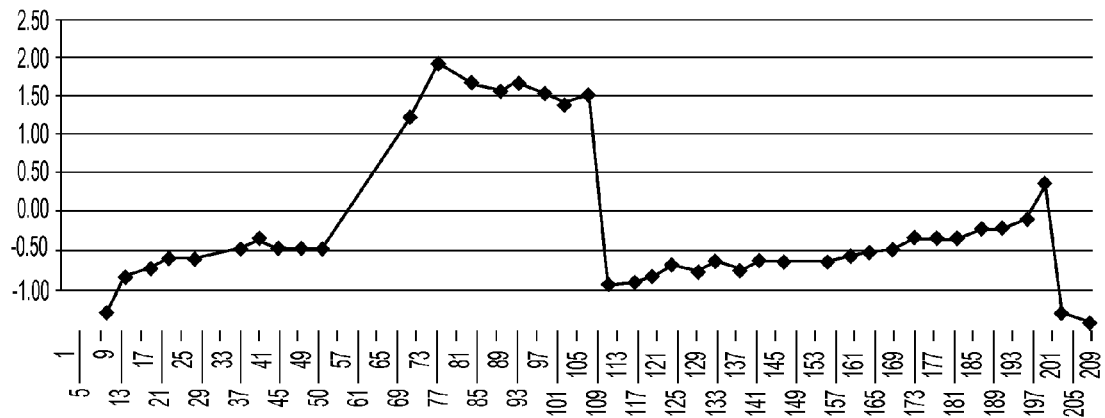
FIGS. 6A-6C are graphs illustrating measuring of variables associated with the determination of a baseline core temperature according to one embodiment of the present invention.
Figure 6B:
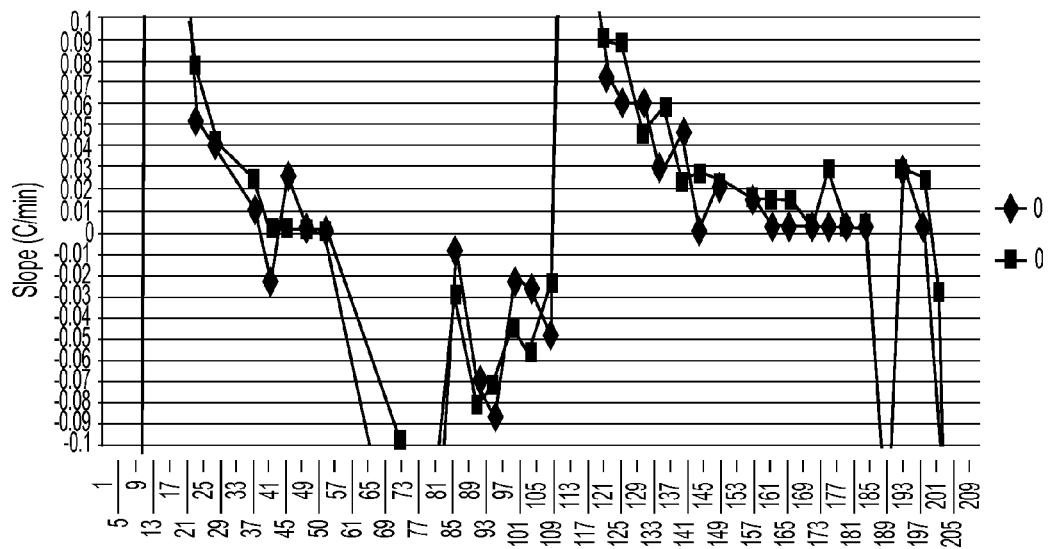
Figure 6C:
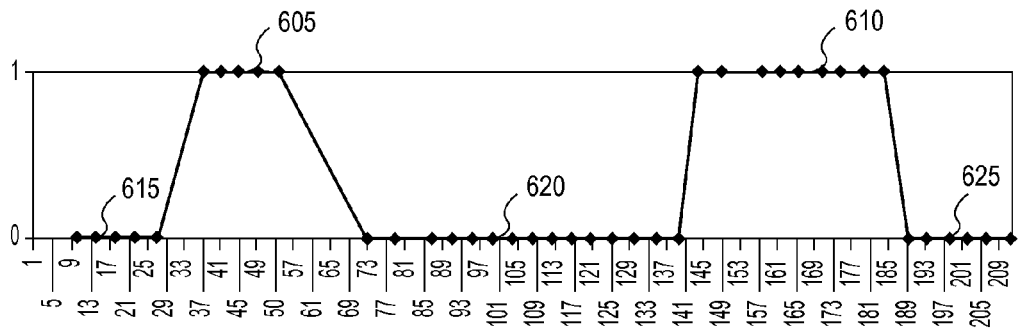

FIGS. 6A-6C are graphs illustrating measuring of variables associated with the determination of a baseline according to one embodiment of the present invention. More specifically, FIGS. 6A-6C includes graphs illustrating the measuring of variables associated with the determination of baseline core temperature in FIG. 5. FIG. 6A shows the difference in temperature between the device's inner (body) and outer (arm) sensors. In instances where the difference between the two sensor readings is less than 0.25° C. in FIG. 5, the temperature recorded by the body facing sensor potentially qualifies as a baseline core temperature. FIG. 6B shows the slope of the graph related to change in both sensor readings. When the slope of the graph related to change in both sensor readings is less than 0.03° C. per minute in FIG. 5, the temperature recorded by the body facing sensor potentially qualifies as a baseline core temperature. FIG. 6C records the determination of a valid baseline core temperature based on the measurements in the first two graphs of FIG. 6A and 6B. When both the temperature difference qualification and the graph slope qualification are met, the validity measurement is 1 (as shown at 605 and 610) and the temperature of the torso facing sensor in FIG. 5 is determined to be a baseline core temperature. Otherwise, the validity measurement is 0 (as shown at 615, 620, and 625) and no baseline core temperature is recorded. At any time the validity measurement is 1, and the temperature is above some predetermined value, for example 38.2 degrees C., the system can declare that a febrile event is occurring. Alternately, any time the validity measurement is 1, and the temperature is higher than a previously established baseline for that patient, for example 1.2 degrees C. above the baseline, the system can declare that a febrile event is occurring. It should be noted that this baseline can be individually calculated for each patient based on previous data and that this baseline can vary throughout a day as it does with natural diurnal temperature cycles.

Figure 7:
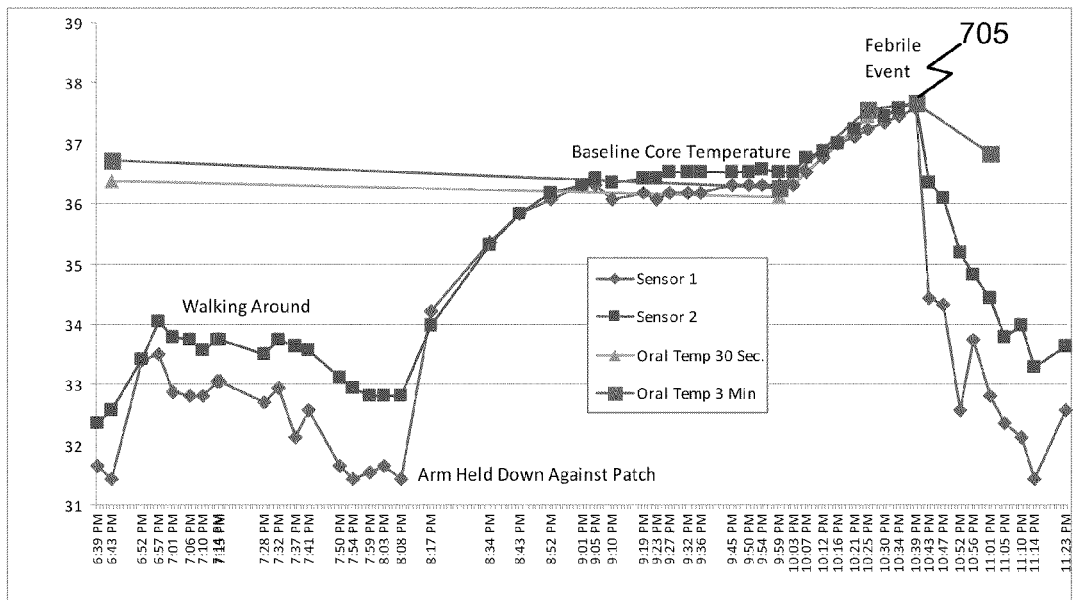
FIG. 7 is a graph illustrating an event that is measured by a change from a valid baseline core temperature according to one embodiment of the present invention.

FIG. 7 is a graph illustrating an event that is measured by a change from a valid baseline according to one embodiment of the present invention. More specifically, FIG. 7 displays a febrile event 705 that is measured by a change from a valid baseline core temperature when the body facing sensor records a temperature increase of greater than 1.2° C. over an existing valid baseline core temperature. Due to the fever causing an increase in temperature over the previously established steady state conditions, a the steady state conditions will not exist, and therefore a validity measurement of 1 will not exist, until a new steady state is reached at the higher temperature caused by the fever. However, a fever can be predicted prior to the temperature measurement reaching a new steady state by extrapolating the curve using non-linear curve fitting regression techniques. The extrapolation may be further refined by smoothing techniques.

FIGS. 5, 6 and 7 describe embodiments where a febrile event is detected during a validity measurement of 1, as previously defined, or as a change in temperature starting from a validity measurement of 1. Depending on the movement of the person, the conditions for having a validity measurement of 1 may exist for a large percent of the time or for only brief periods of time. For bed ridden patients this can be a large percent of the time. It should be noted that in most hospital settings temperatures are typically taken manually only 3 to 6 times per day. It is expected that this system will exceed a validity measurement of 1 more often than this for bed ridden patients. However, it is possible to achieve a prediction of core temperature to a certain probability even when the validity measurement is not 1. This is especially true when the person is well insulated with clothing or bedding and when the insulation of the arm or mattress is only lost for short periods of time.

It should be noted that the errors in temperature reading caused by loss of insulation measure a temperature that is cooler than core temperature. This is true for both inner and outer sensors. Therefore, if any temperature is measured that is above the previously established core temperature baseline, even if the conditions of temperature differential and slope are not met, then this can be considered an above normal temperature. This situation could cause the system to alert caregivers to check that patient, even though an actual febrile event has not been measured.

According to one embodiment, rather than considering sensor data reliable and unreliable based on a comparison of the sensor data being within a predetermined range or other criteria, sensor data can be utilized even if not within range or even at a steady state. In such embodiments, sensor data may be used to build a record or profile for a particular subject and the profile used to validate sensor data or even make predictions based on the sensor data relative to the record or profile. For example, sensor data representing temperature data recorded for a patient as represented above, even transitory data, for example collected after the sensors or the patient moves, can be used to predict the core temperature of the patient by comparing the rate of change of the collected data to similar changes represented in the record or profile. Additionally or alternatively, if the rate of change represented in the collected data is not found to be represented in the record or profile, i.e., the rate of change is outside of expected, errors in the data can be assumed or a problem with the subject, e.g., a fever, can be determined.

Figure 8A:
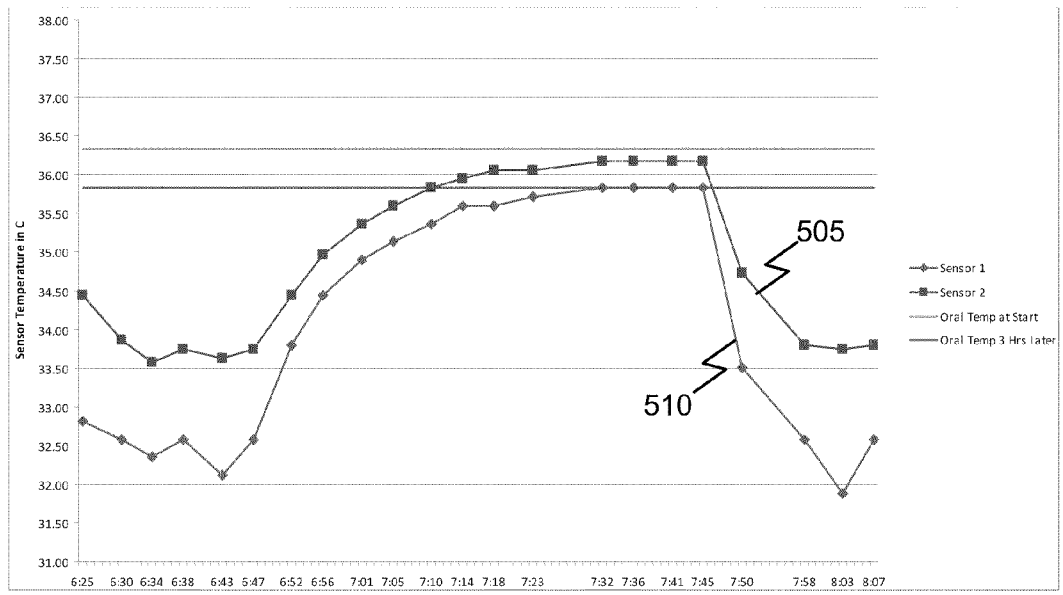
FIGS. 8A and 8B are graphs illustrating a profile of a sensor during a transition period according to one embodiment of the present invention.
Figure 8B:
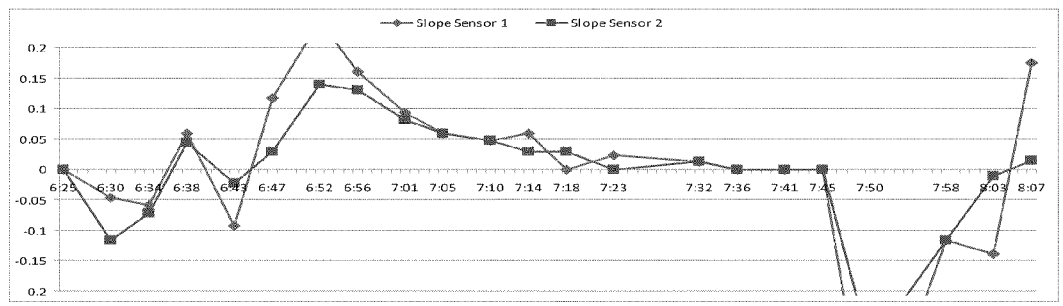

FIGS. 8A and 8B are graphs illustrating a profile of a sensor during a transition period according to one embodiment of the present invention. More specifically, FIGS. 8A and 8B include graphs that illustrate the profile of sensor warm-up in an individual whose arm has been lowered. Warm-up is described as the event that occurs when the slope of the graph of temperatures from the body facing sensor is greater than 0.03° C. per minute and the weighted moving average of the slope of the graph reduces consistently. Warm-up events can be recorded for individuals as a means to establish a warm-up baseline or profile to ultimately enable predicting the onset of fever that occurs during a warm-up event. Warm-up events are recorded as a formula for describing the movement of the weighted moving average of the slope of the graph of sensor 2. These formula can be determined via curve fitting using non-linear regression analysis. Similarity of warm-up events is determined using autocorrelation measurements that result in an autocorrelation of greater than 0.75.

Figure 9:
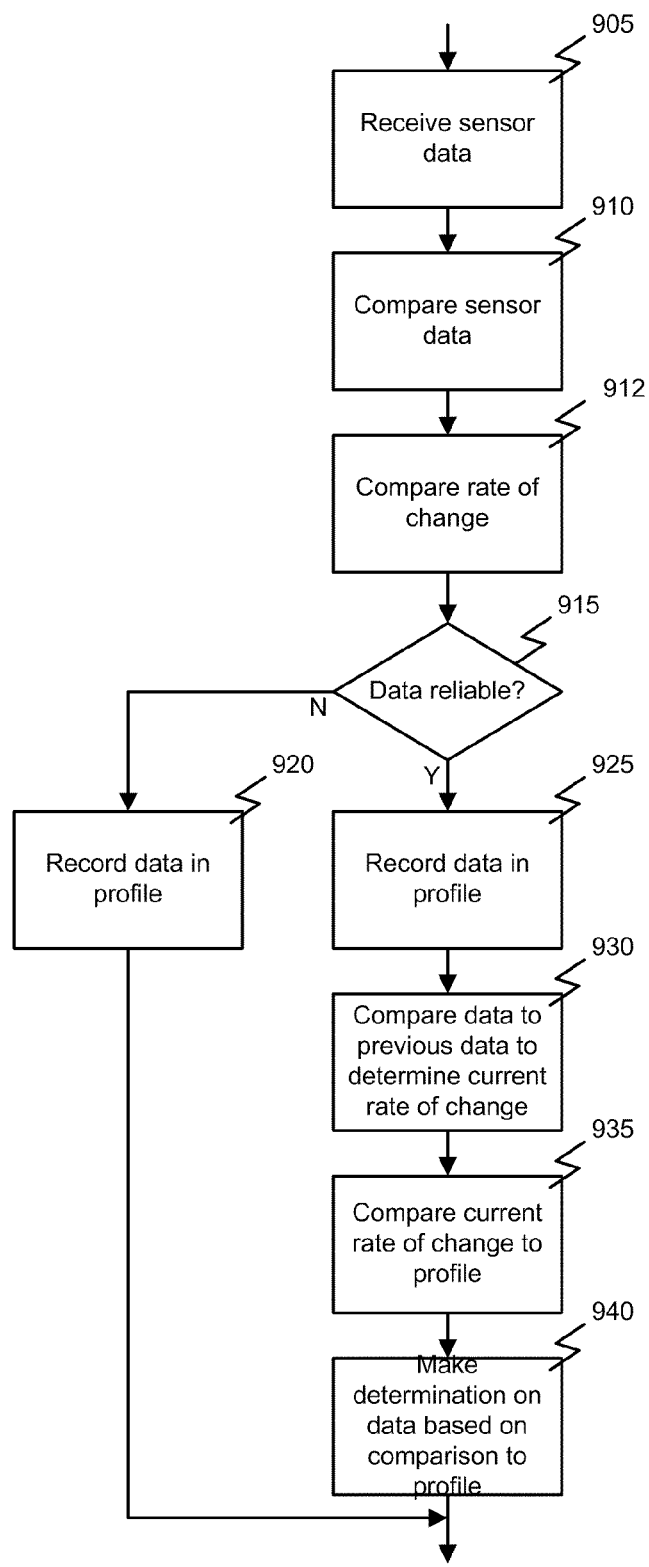
FIG. 9 is a flowchart illustrating a process for remote sensing according to one embodiment of the present invention.

FIG. 9 is a flowchart illustrating a process for remote sensing according to one embodiment of the present invention. In this example, processing begins with receiving 905 sensor data from two or more sensors of a sensing device as described above. The sensor data can be compared 910, one to the others or to previously recorded data 912. Based on this comparison 910 and 912, a determination 915 can be made as whether the data is within acceptable limits. For example, the determination 915 can be based on the differences of the sensor data being within some predefined range and also based on a rate of change between readings that is less than some predefined value. If the sensor data is determined 915 to be within acceptable limits, the data can be recorded 920 and added to a profile for the subject.

If the sensor data is determined 915 to be outside of acceptable limits, the data may still be recorded 925 in the profile but further, a comparison can be made between the current data and a previous data, e.g., a preceding collection point, to determine 930 a current rate of change in the data. This rate of change can then be compared 935 to the profile data, e.g., by comparing the current rate of change to rates recorded in the profile. Based on this comparison, a determination or prediction can be made 940 about the current data and/or the expected data from the subject. For example, if the current rate of change or a rate of change within a predefined difference from the current rate of change is found within the profile, the sensor data can be considered reliable and an expected future data from the profile can be selected and utilized as a current data. Alternatively, if the current rate of change is not found to match any within the profile within the predefined range, the sensor data may be considered unreliable or a determination may be made about the subject. For example, a greater than expected rate of change may be considered to indicate a fever or other problem condition with the subject.

In the foregoing description, for the purposes of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor or logic circuits programmed with the instructions to perform the methods. These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

While illustrative and presently preferred embodiments of the invention have been described in detail herein, it is to be understood that the inventive concepts may be otherwise variously embodied and employed, and that the appended claims are intended to be construed to include such variations, except as limited by the prior art.

What is claimed is:

1. A system for measuring a temperature of a subject, the system comprising:
   a patch including a sensing device with a microcontroller, a wireless transmitter, and a plurality of sensors, the plurality of sensors comprising at least a first temperature sensor and a second temperature sensor;
   a support system comprising a memory, a processor, and a wireless receiver communicatively coupled with the transmitter of the sensing device, wherein the memory comprises a series of instructions which, when executed by the processor, cause the support system:
      to receive sensor data from a sensing device, the sensor data including data from each of the first temperature sensor and the second temperature sensor;
      to compare the received sensor data from the first temperature sensor to the received sensor data from the second temperature sensor;
      to compare the received sensor data to a saved set of previously received sensor data; and
      to determine whether the received sensor data is reliable based on comparing the received sensor data from the first temperature sensor to the received sensor data from the second temperature sensor and comparing the received sensor data to the saved set of previously received sensor data.

2. The system of claim 1, wherein said memory further comprises instructions to compare a rate of change of the received sensor data.

3. The system of claim 2, wherein said memory further comprises instructions to compare the rate of change of the received sensor data to a rate of change recorded in a profile.

4. The system of claim 3, wherein said memory further comprises instructions to determine an occurrence of an event based on comparing the rate of change of the received sensor data to the rate of change recorded in the profile.

5. The system of claim 4, wherein the patch is affixed to a human patient and wherein the event comprises an onset of a fever.

6. The system of claim 1, further comprising a reader device communicatively coupled with the sensing device via the wireless transmitter of the sensing device, wherein the reader device receives temperature data from the sensing device.

7. The system of claim 6, wherein the reader device communicates commands to the sensing device.

8. The system of claim 7, wherein the reader device provides the temperature data to the support system.

* * * * *